(12) United States Patent
Bajaj et al.

(10) Patent No.: US 11,197,921 B2
(45) Date of Patent: Dec. 14, 2021

(54) METHODS FOR MAKING POLYSACCHARIDE-PROTEIN CONJUGATES

(71) Applicant: Merck Sharp & Dohme Corp., Rahway, NJ (US)

(72) Inventors: Jitin Bajaj, Chalfont, PA (US); Michael Albert Winters, Doylestown, PA (US); Emily Wen, Harleysville, PA (US); Jian He, Blue Bell, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/482,349

(22) PCT Filed: Jan. 30, 2018

(86) PCT No.: PCT/US2018/015907
§ 371 (c)(1),
(2) Date: Jul. 31, 2019

(87) PCT Pub. No.: WO2018/144439
PCT Pub. Date: Aug. 9, 2018

(65) Prior Publication Data
US 2020/0046821 A1  Feb. 13, 2020

Related U.S. Application Data

(60) Provisional application No. 62/452,522, filed on Jan. 31, 2017.

(51) Int. Cl.
*A61K 39/09* (2006.01)
*A61K 39/385* (2006.01)
*A61K 39/00* (2006.01)

(52) U.S. Cl.
CPC .......... *A61K 39/092* (2013.01); *A61K 39/385* (2013.01); *A61K 2039/6037* (2013.01); *A61K 2039/62* (2013.01)

(58) Field of Classification Search
CPC ................ A61K 39/092; A61K 39/385; A61K 2039/6037
USPC ...................................................... 424/244.1
See application file for complete search history.

(56) References Cited

U.S. PATENT DOCUMENTS

| | | |
|---|---|---|
| 4,761,283 A | 8/1988 | Anderson et al. |
| 8,192,746 B2 | 6/2012 | Caulfield et al. |
| 8,808,707 B1 | 8/2014 | Siber |
| 9,669,084 B2 | 6/2017 | Siber |
| 10,406,220 B2 | 9/2019 | Siber et al. |
| 2007/0231340 A1 * | 10/2007 | Hausdorff ............... A61P 35/00 424/184.1 |
| 2011/0195086 A1 | 8/2011 | Caulfield et al. |
| 2015/0202309 A1 | 7/2015 | Emini et al. |
| 2015/0231270 A1 | 8/2015 | Prasad |
| 2016/0375118 A1 | 12/2016 | Park et al. |

FOREIGN PATENT DOCUMENTS

| | | |
|---|---|---|
| EP | 477508 B1 | 7/1995 |
| EP | 471177 B1 | 10/1995 |
| EP | 562107 B1 | 5/2002 |
| WO | 1998016198 A1 | 4/1998 |
| WO | 2006110352 A2 | 10/2006 |
| WO | 2006110381 A1 | 10/2006 |
| WO | 2007127665 A2 | 11/2007 |
| WO | 2008045852 A2 | 4/2008 |
| WO | 2008079653 A1 | 7/2008 |
| WO | 2008079732 A2 | 7/2008 |
| WO | 2008118752 A2 | 10/2008 |
| WO | 2008143709 A2 | 11/2008 |
| WO | 2009009629 A1 | 1/2009 |
| WO | 2010080484 A1 | 7/2010 |
| WO | 2010080486 A2 | 7/2010 |
| WO | 2011100151 A1 | 8/2011 |
| WO | 2011151760 A2 | 12/2011 |
| WO | WO2012078482 A1 | 6/2012 |
| WO | 2014097099 A2 | 6/2014 |
| WO | 2015110940 A2 | 7/2015 |
| WO | 2015110941 A2 | 7/2015 |
| WO | 2015110942 A2 | 7/2015 |
| WO | 2016113644 A1 | 7/2016 |

(Continued)

OTHER PUBLICATIONS

Musher et al. Pneumococcal Polysaccharide Vaccine in Young Adults and Older Bronchitics: Determination of IgG Responses by ELISA and the Effect of Adsorption of Serum with Non-iype-Specific Cell Wall Polysaccharide. Journal of Infectious Diseases 1990; 161:728-735. (Year: 1990).*

Contreras, M et al., Characterization of the roles of NikR, a nickel-responsive plelotropic 1-7, 9-18, 19/1, 19/17-18,, Molecular Microbiology, 2003, 947-963, 49(4).

Smith, SW et al, Nickel-Catalyzed Negishi Cross-Couplings of Secondary Nucleophiles with 1, Angewandte Chemie International, 2008, 120: 9474-9476.

Andrews, Nick J. et al., Serotype-specific effectiveness and correlates of protection for the 13-valent pneumococcal conjugate vaccine: a postlicensure indirect cohort study, Lancet Infect. Dis., 2014, 839-846, 14.

(Continued)

*Primary Examiner* — Yih-Horing Shiao
(74) *Attorney, Agent, or Firm* — Matthew A. Leff; Alysia A. Finnegan

(57) ABSTRACT

The present invention provides methods for making polysaccharide-protein conjugates in which polysaccharides, typically from bacteria, are conjugated to a carrier protein by reductive amination under conditions which improve conjugation reaction consistency, increase consumption of protein during conjugation reaction, generate conjugates of higher molecular weight, and/or reduce the levels of free cyanide in the conjugate reaction product. The polysaccharide-protein conjugates obtained using these methods are useful for inclusion in multivalent vaccines.

13 Claims, 1 Drawing Sheet

(56) References Cited

FOREIGN PATENT DOCUMENTS

| WO | 2016178123 | A1 | 11/2016 |
|---|---|---|---|
| WO | 2017013548 | A1 | 1/2017 |
| WO | 2017085586 | A1 | 5/2017 |
| WO | 2017085602 | A1 | 5/2017 |
| WO | 2018134693 | A1 | 7/2018 |
| WO | 2018144438 | A1 | 8/2018 |
| WO | 2018144439 | A1 | 8/2018 |
| WO | 2018156465 | A1 | 8/2018 |
| WO | WO2018156467 | A1 | 8/2018 |
| WO | WO2018156468 | A1 | 8/2018 |
| WO | WO2018156491 | A1 | 8/2018 |
| WO | 2019036313 | A1 | 2/2019 |
| WO | 2019050813 | A1 | 3/2019 |
| WO | 2019050814 | A1 | 3/2019 |
| WO | 2019050815 | A1 | 3/2019 |
| WO | 2019050816 | A1 | 3/2019 |
| WO | 2019050818 | A1 | 3/2019 |
| WO | 2019083865 | A1 | 5/2019 |
| WO | 2019139692 | A2 | 7/2019 |
| WO | 2019212842 | A1 | 11/2019 |
| WO | 2019212844 | A1 | 11/2019 |
| WO | 2019212846 | A1 | 11/2019 |
| WO | 2019217183 | A1 | 11/2019 |
| WO | 2019236435 | A1 | 12/2019 |
| WO | 2020121159 | A1 | 6/2020 |
| WO | 2020131763 | A2 | 6/2020 |
| WO | 2020208502 | A1 | 10/2020 |
| WO | 2020247299 | A1 | 12/2020 |
| WO | 2020247301 | A1 | 12/2020 |

OTHER PUBLICATIONS

Konadu, Edward et al., Synthesis, Characterization, and Immunological Properties in Mice of Conjugates Composed of Detoxified Lipopolysaccharide of *Salmonella paratyphi* A Bound to Tetanus Toxoid, with Emphasis on the Role of O Acetyls, Infection and Immunity, 1996, 2709-2715, 64(7).

Watson, Douglas C. et al., Protection of Mice against *Salmonella typhimunium* with an O-Specific Polysaccharide-Protein Conjugate Vaccine, Infection and Immunity, 1992, 4679-4686, 60(11).

Michael J. Gidley et al., Reductive methylation of proteins with sodium cyanoborohydride, Biochem, 1982, 331-334, 203.

Neil Jentoft et al., Protein Labeling by Reductive Methylation with Sodium Cyanoborohydride: Effect of Cyanide and Metal Ions on the Reaction, Analytical Biochemistry, 1980, 186-190, 106.

* cited by examiner

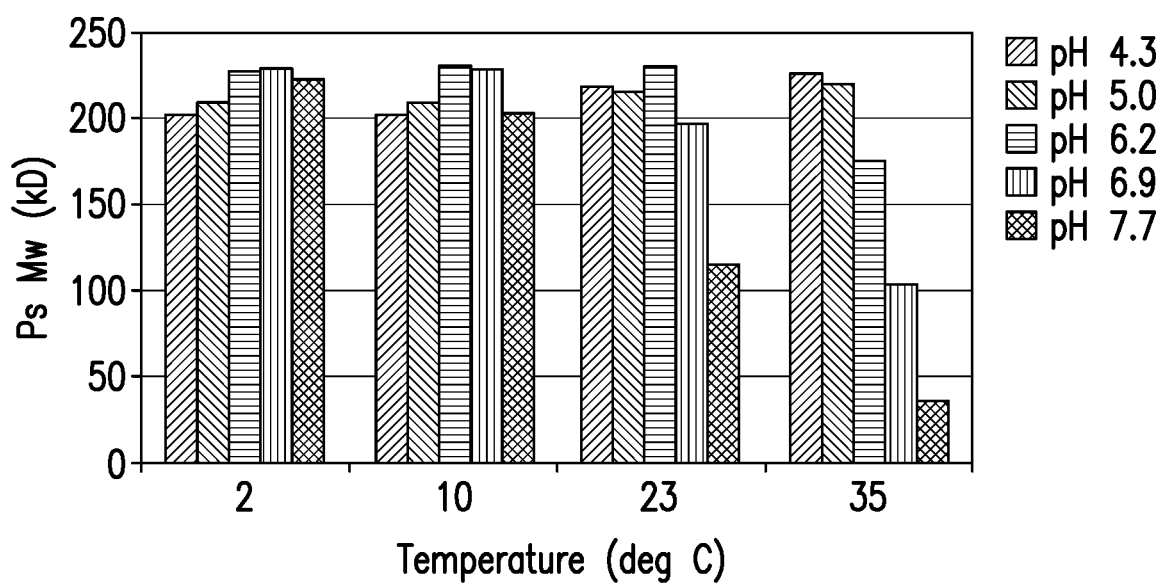

METHODS FOR MAKING POLYSACCHARIDE-PROTEIN CONJUGATES

FIELD OF INVENTION

The present invention provides methods for making polysaccharide-protein conjugates by reductive amination under conditions which enable formation of high molecular weight conjugates and/or maximize consumption of carrier protein. The polysaccharide-protein conjugates obtained using these methods are useful for inclusion in multivalent vaccines.

BACKGROUND OF THE INVENTION

Capsular polysaccharides from bacteria have been used for many years in vaccines as they elicit opsonophagocytic antibodies capable of neutralizing the bacterium. However, most polysaccharides are T-independent antigens, and as a result they are poorly immunogenic in infants and the elderly. Covalent conjugation of polysaccharide to a carrier protein can convert T-independent antigens into T-dependent antigens, thereby enhancing memory responses and allowing protective immunity to develop in these patient populations. The most effective polysaccharide vaccines for infants are therefore based on glycoconjugates.

Various methods are known for the conjugation of polysaccharides to a carrier protein. Some methods involve random activation of the polysaccharide chain (e.g., with 1-cyano-4-dimethylaminopyridinium tetrafluoroborate (CDAP)) prior to conjugation via a linker (see, for example, Watson et al. (1992) Infect Immun. 60(11):4679-86; and Konadu et al. (1996) Infect Immun. (7):2709-15). Methods of reductive amination for conjugating polysaccharides to proteins are disclosed in U.S. Pat. No. 4,761,283, and European Patent Nos. EP 477 508, and EP 562 107.

In either of the described conjugation chemistries, conjugation efficiency and consistency are critical to control the process and product. In particular, conjugates prepared from *Streptococcus pneumoniae* serotype 3 polysaccharide using prior art methods have less than desirable immunogenicity. See, e.g., Andrews et al., 2014, Lancet Infect Dis; 14: 839-46. Thus, there remains a need for further and better ways of preparing conjugates with increased efficiency and consistency.

SUMMARY OF THE INVENTION

The present invention provides methods for preparing polysaccharide-protein conjugates by reductive amination under conditions which enable formation of high molecular weight conjugates and/or maximize consumption of carrier protein. The polysaccharide-protein conjugates obtained using these methods are useful for inclusion in multivalent vaccines.

In a first aspect, the present invention provides a method for producing a polysaccharide protein conjugate, comprising the steps of: a) reacting an activated polysaccharide with a carrier protein in an aqueous buffer in the presence of a cyanoborohydride salt and nickel (II); b) optionally, adding a strong reducing agent; and c) purifying the conjugate reaction mixture to remove unreacted polysaccharide and protein and conjugation reagents. Step a) can be performed at a pH from 6.0 to 8.5, or at a pH of 6.5 to 7.5. The nickel can be in the form of nickel chloride ($NiCl_2$) or nickel sulfate ($NiSO_4$). The nickel can be present at a concentration of 0.5 mM to 15 mM, or from 0.5 mM to 5 mM. In certain embodiments, the nickel is added to the reaction mixture before addition of sodium cyanoborohydride. In certain embodiments, the purification step is effected by ultrafiltration.

The methods described herein for this aspect are applicable to polysaccharides including but not limited to Meningococcal polysaccharides, Pneumococcal polysaccharides, *Hemophilus influenzae* type b polysaccharide, Vi polysaccharide of *Salmonnella typhi*, and group B *Streptococcus* polysaccharides. In certain embodiments of the invention, the polysaccharide is a *Streptococcus pneumoniae* capsular polysaccharide.

In certain embodiments of this aspect, the conjugation reaction temperature is controlled between 10-30° C. or 10-22° C.

In a second aspect, the present invention provides a method for preparing a *Streptococcus pneumoniae* serotype 3 polysaccharide protein conjugate by reductive amination, the method comprising: a) reacting an activated serotype 3 polysaccharide with a carrier protein in an aqueous buffer in the presence of a cyanoborohydride salt at a temperature in a range from 2 to 25° C. and a pH of 7.0 or less or a range from 2 to 10° C. and a pH of 7.7 or less; b) optionally, adding a strong reducing agent; and c) purifying the conjugate reaction mixture to remove residual reactant including free cyanide ions. In certain embodiments, the purification step is effected by ultrafiltration.

In certain embodiments of this aspect, step a) is performed at a pH from 6.0 to 7.0 or 6.2 to 6.9. In certain embodiments of this aspect, the reaction temperature in step a) is in a range from 2 to 23° C., from 4 to 15° C. or from 8 to 12° C.

In one embodiment of either aspect, the cyanoborohydride salt can be sodium cyanoborohydride. In certain embodiments of either aspect, addition of a strong reducing agent is performed. In certain embodiments, the strong reducing agent comprises borohydride ion which can be in the form of sodium borohydride.

In a third aspect, the present invention provides a method for activating a *Streptococcus pneumoniae* serotype 3 polysaccharide by periodate oxidation, the method comprising reacting a serotype 3 polysaccharide with a periodate in an aqueous buffer at a pH in the range from 4.3-6.9 at a temperature in the range from 2-23° C., at a pH in the range from 4.3-7.7 at a temperature in the range from 2-10° C., or at a pH in the range from 4.3-6.2 at a temperature in the range from 2-35° C.

The present invention is also directed to polysaccharide protein conjugates prepared according to the methods described in the first and second aspects one and to activated polysaccharides prepared according to the method described in the third aspect.

The methods described herein are applicable to carrier proteins including but not limited to tetanus toxoid, diphtheria toxoid, and $CRM_{197}$. In certain embodiments of the invention, the carrier protein is $CRM_{197}$.

BRIEF DESCRIPTION OF THE DRAWINGS

FIG. 1 shows serotype 3 polysaccharide size (as determined by HPSEC UV-MALS-RI) after activation with sodium metaperiodate and a 10 hour incubation in solutions varied for pH (pH 4.3, 5.0, 6.2, 6.9, or 7.7 in either 150 mM sodium acetate or 150 mM potassium phosphate) and temperature (2° C., 10° C., 23° C., or 35° C.).

DETAILED DESCRIPTION OF THE INVENTION

The present invention provides improved methods for preparing polysaccharide protein conjugate reaction mixture under conditions which enable formation of high molecular weight conjugates and/or maximize consumption of carrier protein. The polysaccharide protein conjugates are useful as drug substances for inclusion into a multivalent pneumococcal conjugate vaccine.

Without being bound by any theory, in aspect one of the invention, it is believed that the addition of nickel to the conjugation reaction complexes residual, interfering cyanide, thereby increasing the consumption of protein during the conjugation reaction and leading to formation of larger, potentially more immunogenic conjugates.

Without being bound by any theory, in aspect two of the invention, Applicants have demonstrated that outside a specific pH range and temperature range, polysaccharide from serotype 3 is prone to degradation. By performing the activation reaction and/or conjugation reaction within specific parameters for pH and temperature, a larger, potentially more immunogenic serotype 3 polysaccharide-protein conjugate can be obtained.

As used herein, the term "polysaccharide" is meant to include any antigenic saccharide element (or antigenic unit) commonly used in the immunologic and bacterial vaccine arts, including, but not limited to, a "saccharide", an "oligosaccharide", a "polysaccharide", a "liposaccharide", a "lipo-oligosaccharide (LOS)", a "lipopolysaccharide (LPS)", a "glycosylate", a "glycoconjugate" and the like. An "activated polysaccharide" is a polysaccharide which has been chemically modified to be suitable for conjugation to a carrier protein, e.g., by introduction of an aldehyde group.

As used herein, the term "comprises" when used with the immunogenic composition of the invention refers to the inclusion of any other components (subject to limitations of "consisting of" language for the antigen mixture), such as adjuvants and excipients. The term "consisting of" when used with the multivalent polysaccharide-protein conjugate mixture refers to a mixture having those particular *S. pneumoniae* polysaccharide protein conjugates and no other *S. pneumoniae* polysaccharide protein conjugates from a different serotype.

As used herein, ranges used for, for example, pH and temperature, are meant to be inclusive. For example, a pH range from 5.0 to 9.0 is meant to include a pH of 5.0 and a pH of 9.0. Similarly, a temperature range from 4 to 25° C. is meant to include the outer limits of the range, i.e., 4° C. and 25° C.

Capsular Polysaccharides

Bacterial capsular polysaccharides, particularly those that have been used as antigens, are suitable for use in the invention and can readily be identified by methods for identifying immunogenic and/or antigenic polysaccharides. These bacterial capsular polysaccharides may, for example, be from *N. meningitidis*, particularly serogroups A, C, W135 and Y; *S. pneumoniae*, particularly from serotypes: 1, 2, 3, 4, 5, 6A, 6B, 6C, 7C, 7F, 8, 9N, 9V, 10A, 11A, 12F, 14, 15A, 15B, 15C, 16F, 17F, 18C, 19A, 19F, 20, 22F, 23A, 23B, 23F, 24F, 33F, 35B, 35F, or 38; *S. agalactiae*, particularly serotypes Ia, Ib, and III; *S. aureus*, particularly from *S. aureus* type 5 and type 8; *Haemophilus influenzae* Type b; *Salmonella enterica Typhi* Vi; and *Clostridium difficile*.

Non-capsular bacterial polysaccharides may also be suitable for use in the invention. An exemplary non-capsular bacterial polysaccharide is the *S. pyogenes* GAS carbohydrate (also known as the GAS cell wall polysaccharide, or GASP).

Non-bacterial polysaccharides may also be suitable for use in the invention. For example, the invention may use glucans, e.g. from fungal cell walls. Representative glucans include laminarin and curdlan.

The polysaccharides may be used in the form of oligosaccharides. These are conveniently formed by fragmentation of purified polysaccharide (e.g. by chemical hydrolysis or physical shearing), which will usually be followed by purification of the fragments of the desired size.

Polysaccharides can be purified by known techniques. The invention is not limited to polysaccharides purified from natural sources, however, and the polysaccharides may be obtained by other methods, such as total or partial synthesis. Capsular polysaccharides from *S. pneumoniae* can be prepared by standard techniques known to those skilled in the art. For example, polysaccharides can be isolated from bacteria and may be sized to some degree by known methods (see, e.g., European Patent Nos. EP497524 and EP497525); and preferably by microfluidization accomplished using a homogenizer or by chemical hydrolysis. In one embodiment, *S. pneumoniae* strains corresponding to each polysaccharide serotype are grown in a soy-based medium. The individual polysaccharides are then purified through standard steps including centrifugation, precipitation, and ultrafiltration. See, e.g., U.S. Patent Application Publication No. 2008/0286838 and U.S. Pat. No. 5,847,112. Polysaccharides can be sized in order to reduce viscosity and/or to improve filterability and the lot-to-lot consistency of subsequent conjugated products.

The purified polysaccharides can be chemically activated to introduce functionalities capable of reacting with the carrier protein using standard techniques. In one embodiment, the chemical activation of the polysaccharides and subsequent conjugation to the carrier protein are achieved by means described in U.S. Pat. Nos. 4,365,170, 4,673,574 and 4,902,506. Briefly, the pneumococcal polysaccharide is reacted with a periodate-based oxidizing agent such as sodium periodate, potassium periodate, or periodic acid resulting in oxidative cleavage of vicinal hydroxyl groups to generate reactive aldehyde groups. Suitable molar equivalents of periodate (e.g., sodium periodate, sodium metaperiodate and the like) include 0.05 to 0.5 molar equivalents (molar ratio of periodate to polysaccharide repeat unit) or 0.1 to 0.5 molar equivalents. The periodate reaction can be varied from 30 minutes to 24 hours depending on the diol conformation (e.g., acyclic diols, cis diols, trans diols), which controls accessibility of the reactive hydroxyl groups to the sodium periodate.

For the purpose of the present invention, the term "periodate" includes both periodate and periodic acid; the term also includes both metaperiodate ($IO_4^-$) and orthoperiodate ($IO_6^-$) and includes the various salts of periodate (e.g., sodium periodate and potassium periodate). In an embodiment, the capsular polysaccharide is oxidized in the presence of metaperiodate, preferably in the presence of sodium periodate ($NaIO_4$). In another embodiment the capsular polysaccharide is oxidized in the presence of orthoperiodate, preferably in the presence of periodic acid.

Based on the stability data for serotype 3 shown in the Examples, periodate activation can occur at a pH range from 4.3-6.9 and 2-23° C., at a pH in the range from 4.3-7.7 at a temperature in the range from 2-10° C., or at pH range from 4.3-6.2 and 2-35° C. for serotype 3 polysaccharide.

The purified polysaccharides can also be connected to a linker. Once activated or connect to a linker, each capsular polysaccharide is separately conjugated to a carrier protein to form a glycoconjugate. The polysaccharide conjugates may be prepared by known coupling techniques.

The polysaccharide can be coupled to a linker to form a polysaccharide-linker intermediate in which the free terminus of the linker is an ester group. The linker is therefore one in which at least one terminus is an ester group. The other terminus is selected so that it can react with the polysaccharide to form the polysaccharide-linker intermediate.

The polysaccharide can be coupled to a linker using a primary amine group in the polysaccharide. In this case, the linker typically has an ester group at both termini. This allows the coupling to take place by reacting one of the ester groups with the primary amine group in the polysaccharide by nucleophilic acyl substitution. The reaction results in a polysaccharide-linker intermediate in which the polysaccharide is coupled to the linker via an amide linkage. The linker is therefore a bifunctional linker that provides a first ester group for reacting with the primary amine group in the polysaccharide and a second ester group for reacting with the primary amine group in the carrier molecule. A typical linker is adipic acid N-hydroxysuccinimide diester (SIDEA).

The coupling can also take place indirectly, i.e. with an additional linker that is used to derivatize the polysaccharide prior to coupling to the linker.

The polysaccharide can be coupled to the additional linker using a carbonyl group at the reducing terminus of the polysaccharide. This coupling comprises two steps: (a1) reacting the carbonyl group with the additional linker; and (a2) reacting the free terminus of the additional linker with the linker. In these embodiments, the additional linker typically has a primary amine group at both termini, thereby allowing step (a1) to take place by reacting one of the primary amine groups with the carbonyl group in the polysaccharide by reductive amination. A primary amine group is used that is reactive with the carbonyl group in the polysaccharide. Hydrazide or hydroxylamino groups are suitable. The same primary amine group is typically present at both termini of the additional linker which allows for the possibility of polysaccharide (Ps)-Ps coupling. The reaction results in a polysaccharide-additional linker intermediate in which the polysaccharide is coupled to the additional linker via a C—N linkage.

The polysaccharide can be coupled to the additional linker using a different group in the polysaccharide, particularly a carboxyl group. This coupling comprises two steps: (a1) reacting the group with the additional linker; and (a2) reacting the free terminus of the additional linker with the linker. In this case, the additional linker typically has a primary amine group at both termini, thereby allowing step (a1) to take place by reacting one of the primary amine groups with the carboxyl group in the polysaccharide by EDAC activation. A primary amine group is used that is reactive with the EDAC-activated carboxyl group in the polysaccharide. A hydrazide group is suitable. The same primary amine group is typically present at both termini of the additional linker. The reaction results in a polysaccharide-additional linker intermediate in which the polysaccharide is coupled to the additional linker via an amide linkage.

Carrier Protein

In a particular embodiment of the present invention, $CRM_{197}$ is used as the carrier protein. $CRM_{197}$ is a non-toxic variant (i.e., toxoid) of diphtheria toxin. In one embodiment, it is isolated from cultures of *Corynebacterium diphtheria* strain C7 (p197) grown in casamino acids and yeast extract-based medium. In another embodiment, $CRM_{197}$ is prepared recombinantly in accordance with the methods described in U.S. Pat. No. 5,614,382. Typically, $CRM_{197}$ is purified through a combination of ultrafiltration, ammonium sulfate precipitation, and ion-exchange chromatography. In some embodiments, $CRM_{197}$ is prepared in *Pseudomonas fluorescens* using Pfenex Expression Technology™ (Pfenex Inc., San Diego, Calif.).

Other suitable carrier proteins include additional inactivated bacterial toxins such as DT (Diphtheria toxoid), TT (tetanus toxoid) or fragment C of TT, pertussis toxoid, cholera toxoid (e.g., as described in International Patent Application Publication No. WO 2004/083251), *E. coli* LT, *E. coli* ST, and exotoxin A from *Pseudomonas aeruginosa*. Bacterial outer membrane proteins such as outer membrane complex c (OMPC), porins, transferrin binding proteins, pneumococcal surface protein A (PspA; See International Application Patent Publication No. WO 02/091998), pneumococcal surface adhesin protein (PsaA), C5a peptidase from Group A or Group B *streptococcus*, or *Haemophilus influenzae* protein D, pneumococcal pneumolysin (Kuo et al., 1995, Infect Immun 63; 2706-13) including ply detoxified in some fashion for example dPLY-GMBS (See International Patent Application Publication No. WO 04/081515) or dPLY-formol, PhtX, including PhtA, PhtB, PhtD, PhtE and fusions of Pht proteins for example PhtDE fusions, PhtBE fusions (See International Patent Application Publication Nos. WO 01/98334 and WO 03/54007), can also be used. Other proteins, such as ovalbumin, keyhole limpet hemocyanin (KLH), bovine serum albumin (BSA) or purified protein derivative of tuberculin (PPD), PorB (from *N. meningitidis*), PD (*Haemophilus influenzae* protein D; see, e.g., European Patent No. EP 0 594 610 B), or immunologically functional equivalents thereof, synthetic peptides (See European Patent Nos. EP0378881 and EP0427347), heat shock proteins (See International Patent Application Publication Nos. WO 93/17712 and WO 94/03208), pertussis proteins (See International Patent Application Publication No. WO 98/58668 and European Patent No. EP0471177), cytokines, lymphokines, growth factors or hormones (See International Patent Application Publication No. WO 91/01146), artificial proteins comprising multiple human CD4+ T cell epitopes from various pathogen derived antigens (See Falugi et al., 2001, Eur J Immunol 31:3816-3824) such as N19 protein (See Baraldoi et al., 2004, Infect Immun 72:4884-7), iron uptake proteins (See International Patent Application Publication No. WO 01/72337), toxin A or B of *C. difficile* (See International Patent Publication No. WO 00/61761), and flagellin (See Ben-Yedidia et al., 1998, Immunol Lett 64:9) can also be used as carrier proteins.

Where multivalent vaccines are used, a second carrier can be used for one or more of the antigens in a multivalent vaccine. The second carrier protein is preferably a protein that is non-toxic and non-reactogenic and obtainable in sufficient amount and purity. The second carrier protein is also conjugated or joined with an antigen, e.g., a *S. pneumoniae* polysaccharide to enhance immunogenicity of the antigen. Carrier proteins should be amenable to standard conjugation procedures. In one embodiment, each capsular polysaccharide not conjugated to the first carrier protein is conjugated to the same second carrier protein (e.g., each capsular polysaccharide molecule being conjugated to a single carrier protein). In another embodiment, the capsular polysaccharides not conjugated to the first carrier protein are conjugated to two or more carrier proteins (each capsular polysaccharide molecule being conjugated to a single carrier protein). In such embodiments, each capsular polysaccharide of the same serotype is typically conjugated to the same carrier protein. Other DT mutants can be used as the second carrier protein, such as $CRM_{176}$, $CRM_{228}$, $CRM_{45}$ (Uchida et al., 1973, J Biol Chem 218:3838-3844); $CRM_9$, $CRM_{45}$, $CRM_{102}$, $CRM_{103}$ and $CRM_{107}$ and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. Nos. 4,709,017 or 4,950,740; mutation of at least one or more residues Lys 516, Lys 526, Phe 530 and/or Lys 534 and other mutations disclosed in U.S. Pat. Nos. 5,917,017 or 6,455,673; or fragment disclosed in U.S. Pat. No. 5,843,711.

Conjugation by Reductive Amination

Covalent coupling of polysaccharide to carrier protein can be performed via reductive amination in which an amine-reactive moiety on the polysaccharide is directly coupled to primary amine groups (mainly lysine residues) of the protein. As is well known, a reductive amination reaction proceeds via a two step mechanism. First, a Schiff base intermediate, of formula R—CH=N—R', is formed by reaction of an aldehyde group on molecule 1 (R—CHO) with a primary amine group (R'—NH2) on molecule 2. In the second step, the Schiff base is reduced to form an amino compound of formula R—CH2-NH—R'. While many reducing agents are capable of being utilized, most often a highly selective reducing agent such as sodium cyanoborohydride ($NaCNBH_3$) is employed since such reagents will specifically reduce only the imine function of the Schiff base.

Since all the polysaccharides have an aldehyde function at the end of the chain (terminal aldehyde function), the conjugation methods comprising a reductive amination of the polysaccharide can be applied very generally and, when there is no other aldehyde function in the repeating unit (intrachain aldehyde function), such methods make it possible to obtain conjugates in which a polysaccharide molecule is coupled to a single molecule of carrier protein.

A typical reducing agent is cyanoborohydride salt such as sodium cyanoborohydride. The imine-selective reducing agent typically employed is sodium cyanoborohydride, although other cyanoborohydride salts can be used including potassium cyanoborohydride. Differences in starting cyanide levels in sodium cyanoborohydride reagent lots and residual cyanide in the conjugation reaction can lead to inconsistent conjugation performance, resulting in variable product attributes, such as conjugate size and conjugate Ps-to-$CRM_{197}$ ratio. By controlling and/or reducing the free cyanide levels in the final reaction product, conjugation variability can be reduced.

Residual unreacted aldehydes on the polysaccharide are optionally reduced with the addition of a strong reducing agent, such as sodium borohydride. Generally, use of a strong reducing agent is preferred. However, for some polysaccharides, it is preferred to avoid this step. For example, S. pneumoniae serotype 5 contains a ketone group that may react readily with a strong reductant. In this case, it is preferable to bypass the reduction step to protect the antigenic structure of the polysaccharide.

In one aspect, the present invention provides a method for producing a polysaccharide protein conjugate, comprising the steps of: a) reacting an activated polysaccharide with a carrier protein in an aqueous buffer in the presence of a cyanoborohydride salt and nickel (II); b) optionally, adding a strong reducing agent; and c) purifying the conjugate reaction mixture to remove cyanide ions. The conjugation reaction may be performed in aqueous solution. See, e.g., US2015/0231270 A1, EP 0471 177 B1, US2011/0195086 A1. Suitable aqueous solutions include buffers such as sodium phosphate or potassium phosphate. Step a) can be performed at a pH from 6.0 to 8.5, or at a pH of 6.5 to 7.5.

The nickel is preferably in the form of Ni(II) for example, in the form of nickel chloride or nickel sulfate. The nickel is typically present at a concentration of 0.5 mM to 15 mM or 0.5 mM to 5 mM. The nickel can be added before, at the same time as, or after the cyanoborohydride. In a preferred embodiment, the nickel is added before sodium cyanoborohydride.

Nickel complexes with residual, interfering cyanide from the sodium cyanoborohydride reducing agent used for reductive amination. See S Gidley et al., Biochem J. 1982, 203: 331-334; Jentoft et al. Anal Biochem. 1980, 106: 186-190. Inclusion of nickel in the reaction mixture can increase conjugation efficiency by effecting free cyanide removal. Transition metals, including nickel, are known to form stable complexes with cyanide and are known to improve reductive methylation of protein amino groups and formaldehyde with sodium cyanoborohydride (S Gidley et al., Biochem J. 1982, 203: 331-334; Jentoft et al. Anal Biochem. 1980, 106: 186-190). By complexing residual, interfering cyanide, the addition of nickel increases the consumption of protein during the conjugation of and leads to formation of larger, potentially more immunogenic conjugates.

In certain embodiments, addition of a strong reducing agent is performed. In certain embodiments, the strong reducing agent comprises borohydride ion which can be in the form of sodium borohydride.

In certain embodiments, the reaction temperature in the reacting step can be at 10-30° C. or 10-22° C.

For serotype 6B polysaccharide, the methods of the invention can result in serotype 6B polysaccharide protein conjugate from 2000 to 5000 kDa or 3000 to 4000 kDa.

For serotype 3 polysaccharide, it was found that the periodate-activated polysaccharide size-reduced at higher temperatures such as 35° C., particularly when held at a higher pH (pH 7.7). Accordingly, to minimize degradation of serotype 3 polysaccharide during conjugation, the temperature and/or pH of the reaction can be controlled within certain parameters. In one embodiment, an activated serotype 3 polysaccharide can be reacted with a carrier protein in an aqueous buffer in the presence of a cyanoborohydride salt at a temperature in a range from 2 to 25° C. and a pH of 7.0 or less, or a range from 2 to 10° C. and a pH of 7.7 or less. The pH range can be from 6.0 to 7.0 or 6.2 to 6.9. The reaction temperature can be in a range from 2 to 23° C., 4 to 15° C. or from 8 to 12° C.

Following conjugation, the polysaccharide-protein conjugates are purified to remove excess conjugation reagents as well as residual free protein and free polysaccharide by one or more of any techniques well known to the skilled artisan, including concentration/diafiltration operations, ultrafiltration, precipitation/elution, column chromatography, and depth filtration. See, e.g., U.S. Pat. No. 6,146,902. In one embodiment, the purifying step is by ultrafiltration.

Multivalent Polysaccharide-Protein Conjugate Vaccines

In certain embodiments, the immunogenic compositions can comprise capsular polysaccharides from S. pneumoniae serotype selected from at least one of 1, 2, 3, 4, 5, 6A, 6B, 6C, 7C, 7F, 8, 9N, 9V, 10A, 11A, 12F, 14, 15A, 15B, 15C, 16F, 17F, 18C, 19A, 19F, 20, 22F, 23A, 23B, 23F, 24F, 33F, 35B, 35F, or 38 conjugated to one or more carrier proteins. Preferably, saccharides from a particular serotype are not conjugated to more than one carrier protein.

After the individual glycoconjugates are purified, they are compounded to formulate the immunogenic composition of the present invention. These pneumococcal conjugates are prepared by separate processes and bulk formulated into a single dosage formulation.

Pharmaceutical/Vaccine Compositions

The present invention further provides compositions, including pharmaceutical, immunogenic and vaccine compositions, comprising, consisting essentially of, or alternatively, consisting of any of the polysaccharide serotype combinations described above together with a pharmaceutically acceptable carrier and an adjuvant. In one embodiment, the compositions comprise, consist essentially of, or consist of 2 to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 distinct polysaccharide-protein conjugates, wherein each of the conjugates contains a different capsular polysaccharide conjugated to either the first carrier protein or the second carrier protein, and wherein the capsular polysaccharides from at least one of serotypes 1, 2, 3, 4, 5, 6A, 6B, 6C, 7C, 7F, 8, 9N, 9V, 10A, 11A, 12F, 14, 15A, 15B, 15C, 16F, 17F, 18C, 19A, 19F, 20, 22F, 23A, 23B, 23F, 24F, 33F, 35B, 35F, or 38 of *Streptococcus pneumoniae* are conjugated to $CRM_{197}$.

Formulation of the polysaccharide-protein conjugates of the present invention can be accomplished using art-recognized methods. For instance, 15 individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

In a preferred embodiment, the vaccine composition is formulated in L-histidine buffer with sodium chloride.

As defined herein, an "adjuvant" is a substance that serves to enhance the immunogenicity of an immunogenic composition of the invention. An immune adjuvant may enhance an immune response to an antigen that is weakly immunogenic when administered alone, e.g., inducing no or weak antibody titers or cell-mediated immune response, increase antibody titers to the antigen, and/or lowers the dose of the antigen effective to achieve an immune response in the individual. Thus, adjuvants are often given to boost the immune response and are well known to the skilled artisan. Suitable adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (defined below) or bacterial cell wall components), such as, for example, (a) MF59 (International Patent Application Publication No. WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, Mass.), (b) SAF, containing 10% Squalene, 0.4% Tween 80, 5% pluronic-blocked polymer L121, and thr-MDP either microfluidized into a submicron emulsion or vortexed to generate a larger particle size emulsion, (c) Ribi™ adjuvant system (RAS), (Corixa, Hamilton, Mont.) containing 2% Squalene, 0.2% Tween 80, and one or more bacterial cell wall components from the group consisting of 3-O-deaylated monophosphorylipid A (MPL™) described in U.S. Pat. No. 4,912,094, trehalose dimycolate (TDM), and cell wall skeleton (CWS), preferably MPL+CWS (Detox™); and (d) a Montanide ISA;

(3) saponin adjuvants, such as Quil A or STIMULON™ QS-21 (Antigenics, Framingham, Mass.) (see, e.g., U.S. Pat. No. 5,057,540) may be used or particles generated therefrom such as ISCOM (immunostimulating complexes formed by the combination of cholesterol, saponin, phospholipid, and amphipathic proteins) and Iscomatrix® (having essentially the same structure as an ISCOM but without the protein);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-tetradecanoyloxytetradecanoylamino]ethyl 2-Deoxy-4-O-phosphono-3-O—[(R)-3-tetradecanoyloxytetradecanoyl]-2-[(R)-3-tetradecanoyloxytetradecanoylamino]-b-D-glucopyranoside, which is also known as 529 (formerly known as RC529), which is formulated as an aqueous form or as a stable emulsion (5) synthetic polynucleotides such as oligonucleotides containing CpG motif(s) (U.S. Pat. No. 6,207,646); and (6) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc.; and (7) complement, such as a trimer of complement component C3d.

In another embodiment, the adjuvant is a mixture of 2, 3, or more of the above adjuvants, e.g., SBAS2 (an oil-in-water emulsion also containing 3-deacylated monophosphoryl lipid A and QS21).

Muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), etc.

In certain embodiments, the adjuvant is an aluminum salt. The aluminum salt adjuvant may be an alum-precipitated vaccine or an alum-adsorbed vaccine. Aluminum-salt adjuvants are well known in the art and are described, for example, in Harlow, E. and D. Lane (1988; Antibodies: A Laboratory Manual Cold Spring Harbor Laboratory) and Nicklas, W. (1992; Aluminum salts. Research in Immunology 143:489-493). The aluminum salt includes, but is not limited to, hydrated alumina, alumina hydrate, alumina trihydrate (ATH), aluminum hydrate, aluminum trihydrate, alhydrogel, Superfos, Amphogel, aluminum (III) hydroxide, aluminum hydroxyphosphate sulfate (Aluminum Phosphate Adjuvant (APA)), amorphous alumina, trihydrated alumina, or trihydroxyaluminum.

APA is an aqueous suspension of aluminum hydroxyphosphate. APA is manufactured by blending aluminum chloride and sodium phosphate in a 1:1 volumetric ratio to precipitate aluminum hydroxyphosphate. After the blending process, the material is size-reduced with a high-shear mixer to achieve a monodisperse particle size distribution. The product is then diafiltered against physiological saline and sterilized (either steam sterilization or autoclaving).

In certain embodiments, a commercially available $Al(OH)_3$ (e.g. Alhydrogel or Superfos of Denmark/Accurate Chemical and Scientific Co., Westbury, N.Y.) is used to adsorb proteins. Adsorption of protein is dependent, in another embodiment, on the pI (Isoelectric pH) of the protein and the pH of the medium. A protein with a lower pI adsorbs to the positively charged aluminum ion more strongly than a protein with a higher pI. Aluminum salts may establish a depot of antigen that is released slowly over a period of 2-3 weeks, be involved in nonspecific activation of macrophages and complement activation, and/or stimulate innate immune mechanism (possibly through stimulation of uric acid). See, e.g., Lambrecht et al., 2009, Curr Opin Immunol 21:23.

Monovalent bulk aqueous conjugates are typically blended together and diluted to target 8 µg/mL for all serotypes except 6B, which will be diluted to target 16 µg/mL. Once diluted, the batch will be filter sterilized, and an equal volume of aluminum phosphate adjuvant added aseptically to target a final aluminum concentration of 250 µg/mL. The adjuvanted, formulated batch will be filled into single-use, 0.5 mL/dose vials.

In certain embodiments, the adjuvant is a CpG-containing nucleotide sequence, for example, a CpG-containing oligonucleotide, in particular, a CpG-containing oligodeoxynucleotide (CpG ODN). In another embodiment, the adjuvant is ODN 1826, which may be acquired from Coley Pharmaceutical Group.

"CpG-containing nucleotide," "CpG-containing oligonucleotide," "CpG oligonucleotide," and similar terms refer to a nucleotide molecule of 6-50 nucleotides in length that contains an unmethylated CpG moiety. See, e.g., Wang et al., 2003, Vaccine 21:4297. In another embodiment, any other art-accepted definition of the terms is intended. CpG-containing oligonucleotides include modified oligonucleotides using any synthetic internucleoside linkages, modified base and/or modified sugar.

Methods for use of CpG oligonucleotides are well known in the art and are described, for example, in Sur et al., 1999, J Immunol. 162:6284-93; Verthelyi, 2006, Methods Mol Med. 127:139-58; and Yasuda et al., 2006, Crit Rev Ther Drug Carrier Syst. 23:89-110.

Administration/Dosage

The compositions and formulations of the present invention can be used to protect or treat a human susceptible to infection, e.g., a pneumococcal infection, by means of administering the vaccine via a systemic or mucosal route. In one embodiment, the present invention provides a method of inducing an immune response to a *S. pneumoniae* capsular polysaccharide conjugate, comprising administering to a human an immunologically effective amount of an immunogenic composition of the present invention. In another embodiment, the present invention provides a method of vaccinating a human against a pneumococcal infection, comprising the step of administering to the human an immunologically effective amount of an immunogenic composition of the present invention.

Optimal amounts of components for a particular vaccine can be ascertained by standard studies involving observation of appropriate immune responses in subjects. For example, in another embodiment, the dosage for human vaccination is determined by extrapolation from animal studies to human data. In another embodiment, the dosage is determined empirically.

"Effective amount" of a composition of the invention refers to a dose required to elicit antibodies that significantly reduce the likelihood or severity of infectivity of a microbe, e.g., *S. pneumonia*, during a subsequent challenge.

The methods of the invention can be used for the prevention and/or reduction of primary clinical syndromes caused by microbes, e.g., *S. pneumonia*, including both invasive infections (meningitis, pneumonia, and bacteremia), and noninvasive infections (acute otitis media, and sinusitis).

Administration of the compositions of the invention can include one or more of: injection via the intramuscular, intraperitoneal, intradermal or subcutaneous routes; or via mucosal administration to the oral/alimentary, respiratory or genitourinary tracts. In one embodiment, intranasal administration is used for the treatment of pneumonia or otitis media (as nasopharyngeal carriage of pneumococci can be more effectively prevented, thus attenuating infection at its earliest stage).

The amount of conjugate in each vaccine dose is selected as an amount that induces an immunoprotective response without significant, adverse effects. Such amount can vary depending upon the pneumococcal serotype. Generally, for polysaccharide-based conjugates, each dose will comprise 0.1 to 100 µg of each polysaccharide, particularly 0.1 to 10 µg, and more particularly 1 to 5 µg. For example, each dose can comprise 100, 150, 200, 250, 300, 400, 500, or 750 ng or 1, 1.5, 2, 3, 4, 5, 6, 7, 7.5, 8, 9, 10, 11, 12, 13, 14, 15, 16, 18, 20, 22, 25, 30, 40, 50, 60, 70, 80, 90, or 100 µg.

In one embodiment, the dose of the aluminum salt is 10, 15, 20, 25, 30, 50, 70, 100, 125, 150, 200, 300, 500, or 700 µg, or 1, 1.2, 1.5, 2, 3, 5 mg or more. In yet another embodiment, the dose of alum salt described above is per µg of recombinant protein.

According to any of the methods of the present invention and in one embodiment, the subject is human. In certain embodiments, the human patient is an infant (less than 1 year of age), toddler (approximately 12 to 24 months), or young child (approximately 2 to 5 years). In other embodiments, the human patient is an elderly patient (>65 years). The compositions of this invention are also suitable for use with older children, adolescents and adults (e.g., aged 18 to 45 years or 18 to 65 years).

In one embodiment of the methods of the present invention, a composition of the present invention is administered as a single inoculation. In another embodiment, the vaccine is administered twice, three times or four times or more, adequately spaced apart. For example, the composition may be administered at 1, 2, 3, 4, 5, or 6 month intervals or any combination thereof. The immunization schedule can follow that designated for pneumococcal vaccines. For example, the routine schedule for infants and toddlers against invasive disease caused by *S. pneumoniae* is 2, 4, 6 and 12-15 months of age. Thus, in a preferred embodiment, the composition is administered as a 4-dose series at 2, 4, 6, and 12-15 months of age.

The compositions of this invention may also include one or more proteins from *S. pneumoniae*. Examples of *S. pneumoniae* proteins suitable for inclusion include those identified in International Patent Application Publication Nos. WO 02/083855 and WO 02/053761.

Formulations

The compositions of the invention can be administered to a subject by one or more method known to a person skilled in the art, such as parenterally, transmucosally, transdermally, intramuscularly, intravenously, intra-dermally, intranasally, subcutaneously, intra-peritoneally, and formulated accordingly.

In one embodiment, compositions of the present invention are administered via epidermal injection, intramuscular injection, intravenous, intra-arterial, subcutaneous injection, or intra-respiratory mucosal injection of a liquid preparation. Liquid formulations for injection include solutions and the like.

The composition of the invention can be formulated as single dose vials, multi-dose vials or as pre-filled syringes.

In another embodiment, compositions of the present invention are administered orally, and are thus formulated in a form suitable for oral administration, i.e., as a solid or a liquid preparation. Solid oral formulations include tablets, capsules, pills, granules, pellets and the like. Liquid oral formulations include solutions, suspensions, dispersions, emulsions, oils and the like.

Pharmaceutically acceptable carriers for liquid formulations are aqueous or nonaqueous solutions, suspensions, emulsions or oils. Examples of nonaqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

The pharmaceutical composition may be isotonic, hypotonic or hypertonic. However it is often preferred that a pharmaceutical composition for infusion or injection is essentially isotonic, when it is administrated. Hence, for storage the pharmaceutical composition may preferably be isotonic or hypertonic. If the pharmaceutical composition is hypertonic for storage, it may be diluted to become an isotonic solution prior to administration.

The isotonic agent may be an ionic isotonic agent such as a salt or a non-ionic isotonic agent such as a carbohydrate. Examples of ionic isotonic agents include but are not limited to sodium chloride (NaCl), calcium chloride ($CaCl_2$), potassium chloride (KCl) and magnesium chloride ($MgCl_2$). Examples of non-ionic isotonic agents include but are not limited to mannitol, sorbitol and glycerol.

It is also preferred that at least one pharmaceutically acceptable additive is a buffer. For some purposes, for example, when the pharmaceutical composition is meant for infusion or injection, it is often desirable that the composition comprises a buffer, which is capable of buffering a solution to a pH in the range of 4 to 10, such as 5 to 9, for example 6 to 8.

The buffer may for example be selected from the group consisting of TRIS, acetate, glutamate, lactate, maleate, tartrate, phosphate, citrate, carbonate, glycinate, histidine, glycine, succinate and triethanolamine buffer.

The buffer may furthermore for example be selected from USP compatible buffers for parenteral use, in particular, when the pharmaceutical formulation is for parenteral use. For example the buffer may be selected from the group consisting of monobasic acids such as acetic, benzoic, gluconic, glyceric and lactic; dibasic acids such as aconitic, adipic, ascorbic, carbonic, glutamic, malic, succinic and tartaric, polybasic acids such as citric and phosphoric; and bases such as ammonia, diethanolamine, glycine, triethanolamine, and TRIS.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, glycols such as propylene glycols or polyethylene glycol, are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

The formulations of the invention may also contain a surfactant. Preferred surfactants include, but are not limited to: the polyoxyethylene sorbitan esters surfactants (commonly referred to as the Tweens); copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy) polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate.

Preferred amounts of surfactants (% by weight) are: polyoxyethylene sorbitan esters (such as PS80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

The formulation also contains a pH-buffered saline solution. The buffer may, for example, be selected from the group consisting of TRIS, acetate, glutamate, lactate, maleate, tartrate, phosphate, citrate, carbonate, glycinate, histidine, glycine, succinate, HEPES (4-(2-hydroxyethyl)-1-piperazineethanesulfonic acid), MOPS (3-(N-morpholino) propanesulfonic acid), MES (2-(N-morpholino)ethanesulfonic acid) and triethanolamine buffer. The buffer is capable of buffering a solution to a pH in the range of 4 to 10, 5.2 to 7.5, or 5.8 to 7.0. In certain aspect of the invention, the buffer selected from the group consisting of phosphate, succinate, histidine, MES, MOPS, HEPES, acetate or citrate. The buffer may furthermore, for example, be selected from USP compatible buffers for parenteral use, in particular, when the pharmaceutical formulation is for parenteral use. The concentrations of buffer will range from 1 mM to 50 mM or 5 mM to 50 mM. In certain aspects, the buffer is histidine at a final concentration of 5 mM to 50 mM, or succinate at a final concentration of 1 mM to 10 mM. In certain aspects, the histidine is at a final concentration of 20 mM±2 mM.

While the saline solution (i.e., a solution containing NaCl) is preferred, other salts suitable for formulation include but are not limited to, $CaCl_2$, KCl and $MgCl_2$ and combinations thereof. Non-ionic isotonic agents including but not limited to sucrose, trehalose, mannitol, sorbitol and glycerol may be used in lieu of a salt. Suitable salt ranges include, but not are limited to 25 mM to 500 mM or 40 mM to 170 mM. In one aspect, the saline is NaCl, optionally present at a concentration from 20 mM to 170 mM.

In a preferred embodiment, the formulations comprise a L-histidine buffer with sodium chloride.

In another embodiment, the pharmaceutical composition is delivered in a controlled release system. For example, the agent can be administered using intravenous infusion, a transdermal patch, liposomes, or other modes of administration. In another embodiment, polymeric materials are used; e.g. in microspheres in or an implant.

The compositions of this invention may also include one or more proteins from *S. pneumoniae*. Examples of *S. pneumoniae* proteins suitable for inclusion include those identified in International Patent Application Publication Nos. WO 02/083855 and WO 02/053761. Having described various embodiments of the invention with reference to the accompanying description and drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLES

Analytical Methods
Molecular Weight and Concentration Analysis of Conjugates Using HPSEC/UV/MALS/RI Assay Polysaccharide and conjugate samples were injected and separated by high performance size-exclusion chromatography (HPSEC). Detection was accomplished with ultraviolet (UV), multi-angle light scattering (MALS) and refractive index (RI) detectors in series. Protein concentration was calculated from UV280 using an extinction coefficient. Free protein was resolved from conjugated protein, enabling the calculation of percent conjugated protein (Tables 1-3). Polysaccharide concentration was deconvoluted from the RI signal (contributed by both protein and polysaccharide) using the dn/dc factors which are the change in a solution's refractive index with a change in the solute concentration reported in mL/g. Average molecular weight of the samples were calculated by Astra software (Wyatt Technology Corporation, Santa Barbara, Calif.) using the measured concentration and light scattering information across the entire sample peak. There are multiple forms of average values of molecular weight for polydispersed molecules. For example, number-average molecular weight Mn, weight-average molecular weight Mw, and z-average molecular weight Mz (Molecules, 2015, 20, 10313-10341). Unless specified, the molecular weights are weight-average molecular weight.

Free Polysaccharide Testing

Free polysaccharide (polysaccharide that is not conjugated with $CRM_{197}$) in conjugate sample was measured by first precipitating free protein and conjugates with deoxycholate (DOC) and hydrochloric acid. Precipitates were then filtered out and the filtrates were analyzed for free polysaccharide concentration by HPSEC/UV/MALS/RI. Free polysaccharide is calculated as a percentage of total polysaccharide measured by HPSEC/UV/MALS/RI.

Cyanide Assay

Samples are adjusted to basic pH and then filtered through a 30 kDa molecular weight cut-off membrane to remove the conjugated protein from the solution. Taurine and naphthalene-2,3-dicarboxaldehyde (NDA), which together react with cyanide to generate a fluorescent product, are added to each sample. Samples are analyzed by reverse phase HPLC with fluorescence detection and cyanide concentration is determined for each sample by comparison to a standard curve.

Example 1: Preparation of *S. Pneumoniae* Capsular Polysaccharides

Methods of culturing pneumococci are well known in the art. See, e.g., Chase, 1967, Methods of Immunology and Immunochemistry 1:52. Methods of preparing pneumococcal capsular polysaccharides are also well known in the art. See, e.g., European Patent No. EP0497524. Isolates of pneumococcal subtypes are available from the American Type Culture Collection (Manassas, Va.). The bacteria are identified as encapsulated, non-motile, Gram-positive, lancet-shaped diplococci that are alpha-hemolytic on blood-agar. Subtypes can be differentiated on the basis of Quelling reaction using specific antisera. See, e.g., U.S. Pat. No. 5,847,112.

Cell banks representing each of the *S. pneumococcus* serotypes present were obtained from the Merck Culture Collection (Rahway, N.J.) in a frozen vial. A thawed seed culture was transferred to the seed fermenter containing a pre-sterilized growth media appropriate for *S. pneumoniae*. The culture was grown in the seed fermenter with temperature and pH control. The entire volume of the seed fermenter was transferred to a production fermenter containing pre-sterilized growth media. The production fermentation was the final cell growth stage of the process. Temperature, pH, and the agitation rate were controlled.

The fermentation process was terminated via the addition of an inactivating agent. After inactivation, the batch was transferred to the inactivation tank where it was held at controlled temperature and agitation. Cell debris was removed using a combination of centrifugation and filtration. The batch was ultrafiltered and diafiltered. The batch was then subjected to solvent-based fractionations that remove impurities and recover polysaccharide.

Example 2: Conjugation of Serotypes 1, 3, 4, 5, 6A, 6B, 7F, 9V, 14, 18C, 19A, 19F, 22F, 23F, and 33F to $CRM_{197}$ Using Reductive Amination in Aqueous Solution The different serotype polysaccharides were individually conjugated to purified $CRM_{197}$ carrier protein using a common process flow. Polysaccharide was dissolved, size reduced, chemically activated and buffer-exchanged by ultrafiltration. Purified $CRM_{197}$ was then conjugated to the activated polysaccharide utilizing $NiCl_2$ (2 mM) in the reaction mixture, and the resulting conjugate was purified by ultrafiltration prior to a final 0.2-micron filtration. Several process parameters within each step, such as pH, temperature, concentration, and time were controlled to serotype-specific values as described in the sections below.

Polysaccharide Size Reduction and Activation

Purified pneumococcal capsular Ps powder was dissolved in water, and all serotypes, except serotype 19A, were 0.45-micron filtered. All serotypes, except serotype 19A, were homogenized to reduce the molecular mass of the Ps. Serotype 19A was not size reduced due to its relatively low starting size. Homogenization pressure and number of passes through the homogenizer were controlled to serotype-specific targets (150-1000 bar; 4-7 passes) to achieve a serotype-specific molecular mass. Serotype 3 was homogenized at 360-400 bar for approximately 5 passes. Size-reduced polysaccharide was 0.2-micron filtered and then concentrated and diafiltered against water using a 10 kDa NMWCO tangential flow ultrafiltration membrane.

The polysaccharide solution was then adjusted to a serotype-specific temperature (4-22° C.) and pH (4-5) with sodium acetate buffer to minimize Ps size reduction during the activation step. Polysaccharide activation was performed via periodate oxidation. For serotype 4, prior to activation, the batch was incubated at approximately 50° C. and pH 4 to partially deketalize the Ps. Ps activation was initiated with the addition of a sodium metaperiodate solution. The amount of sodium metaperiodate added was serotype-specific, ranging from approximately 0.1 to 0.5 moles of sodium metaperiodate per mole of polysaccharide repeating unit. The serotype-specific charge of sodium metaperiodate was selected to achieve a target level of Ps activation (moles aldehyde per mole of Ps repeating unit). Serotype 3 was activated for 6-15 hours at approximately 22° C.

For all serotypes, with the exception of serotypes 5 and 7F, the activated product was diafiltered against 10 mM potassium phosphate, pH 6.4, using a 10 kDa NMWCO tangential flow ultrafiltration membrane. Serotypes 5 and 7F were diafiltered against 10 mM sodium acetate, pH 4-5. Ultrafiltration for all serotypes was conducted at 2-8° C.

Polysaccharide Conjugation to $CRM_{197}$

Oxidized polysaccharide solution was mixed with water and 1.5 M potassium phosphate buffer, either pH 6.0 or pH 7.0, depending on the serotype. The buffer pH was selected to optimize stability of activated Ps during the conjugation reaction. Purified $CRM_{197}$, obtained through expression in *Pseudomonas fluorescens* as previously described (WO 2012/173876 A1), was 0.2-micron filtered and combined with the buffered polysaccharide solution at a polysaccharide to $CRM_{197}$ mass ratio ranging from 0.4 to 1.0 w/w depending on the serotype. The mass ratio was selected to control the polysaccharide to $CRM_{197}$ ratio in the resulting conjugate. The polysaccharide and phosphate concentrations were serotype-specific, ranging from 3.6 to 10.0 g/L and 100 to 150 mM, respectively, depending on the serotype. The serotype-specific Ps concentration was selected to control the size of the resulting conjugate. The solution was then 0.2-micron filtered, and the solution temperature was adjusted to either 10° C. or 22° C. depending on the serotype. The temperature was selected to optimize stability of activated Ps during the conjugation reaction. Nickel chloride was then added to approximately 2 mM using a 100 mM nickel chloride solution. Sodium cyanoborohydride (2 moles per mole of polysaccharide repeating unit) was added. Conjugation proceeded for a serotype-specific duration (72 to 120 hours) in order to maximize consumption of Ps and protein. Serotype 3 was conjugated using polysaccharide and protein concentrations of approximately 4.1 g/L and 6.8 g/L, respectively, at 8-12° C. in 150 mM potassium phosphate, pH 6 buffer.

Reduction with Sodium Borohydride

Following the conjugation reaction, the batch was diluted to a Ps concentration of approximately 3.5 g/L, cooled to 2-8° C., and 1.2-micron filtered. All serotypes (except serotype 5) were diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g Ps/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was then added. Serotype 5 was diafiltered against 300 mM sodium bicarbonate, pH 9 using a 100 kDa NMWCO tangential flow ultrafiltration membrane.

Sterile Filtration and Product Storage

The batch was then concentrated and diafiltered against 10 mM histidine in 150 mM sodium chloride, pH 7.0 at 4° C. using a 300 kDa NMWCO tangential flow ultrafiltration membrane. The retentate batch was 0.2-micron filtered.

Serotype 19F was incubated for approximately 7 days at 22° C., diafiltered against 10 mM histidine in 150 mM sodium chloride, pH 7.0 at 4° C. using a 100 kDa NMWCO tangential flow ultrafiltration membrane, and 0.2-micron filtered.

The batch was adjusted to a Ps concentration of 1.0 g/L with additional 10 mM histidine in 150 mM sodium chloride, pH 7.0. The batch was dispensed into aliquots and frozen at ≤−60° C.

Example 3: Conjugation Studies Using Nickel to Improve Reductive Amination with Sodium Cyanoborohydride as Reducing Agent Differences in starting cyanide levels in 5 M sodium cyanoborohydride reagent lots led to inconsistent conjugation performance, resulting in variable product attributes, such as conjugate size and conjugate Ps-to-$CRM_{197}$ ratio. As shown in Table 1 for Serotype 6B conjugation reactions, the extent of the conjugation was greater, as measured by the larger conjugate size and the higher percentage of conjugated $CRM_{197}$, when there was less cyanide ($CN^-$) in the 5 M sodium cyanoborohydride ($NaCNBH_3$) reagent. Furthermore, upon spiking potassium cyanide (KCN) into the conjugation reaction, the extent of conjugation was reduced. Conjugate size, conjugate Ps-to-$CRM_{197}$ ratio, and the percentage of conjugated $CRM_{197}$ were measured using high-performance-size-exclusion chromatography with ultraviolet, multi-angle-light-scattering, and refractive-index detectors.

TABLE 1

Effect of residual cyanide concentration on serotype 6B-$CRM_{197}$ conjugation

| 5M $NaCNBH_3$ Reagent Lot Identity | Starting $CN^-$ Conc. (mM) in 5M $NaCNBH_3$ | KCN Conc. (mM) Spiked into Conjugation Reaction | Total $CN^-$ Conc. (mM) in Conjugation Reaction | Conjugate Size (kDa) | Conjugate Ps-to-$CRM_{197}$ ratio (w:w) | Percent Conjugated $CRM_{197}$ (%) |
|---|---|---|---|---|---|---|
| A | 43 | 0 | 0.17 | 2550 | 1.1 | 47 |
| B | 250 | 0 | 0.98 | 1400 | 1.7 | 30 |
| A | 43 | 0.81 | 0.98 | 1600 | 1.5 | 33 |

Transition metals form stable complexes with cyanide and are known to improve reductive methylation of protein amino groups and formaldehyde with sodium cyanoborohydride (S Gidley et al., *Biochem J.* 1982, 203: 331-334; Jentoft et al. *Anal Biochem.* 1980, 106: 186-190). However such effect was never studied for reductive amination between carrier protein and high molecular weight activated polysaccharides to form highly branched conjugated products. The impact of residual levels of cyanide in reaction between high molecular weight molecules was also not well understood. The preferred Ni (II) concentration was also not well understood. Therefore, studies were done on the effect of adding soluble Ni (II) to the conjugation reaction prior to the addition of sodium cyanoborohydride. Ni (II) increased the extent of conjugation. Furthermore, the presence of Ni (II) eliminated the effect of starting cyanide level on the extent of serotype 6B conjugation in studies using three lots of 5 M sodium cyanoborohydride (Table 2) with varying levels of cyanide (43-250 mM). In this study, the quality attributes of conjugate size and conjugate Ps-to-$CRM_{197}$ ratio showed no significant variability.

TABLE 2

Effect of 1.5 mM nickel metal ions (Ni (II)) on serotype 6B-$CRM_{197}$ conjugation

| 5M $NaCNBH_3$ Reagent Lot Identity | Starting $CN^-$ Concentration (mM) in 5M $NaCNBH_3$ | Total $CN^-$ conc. (mM) in conjugation reaction | Ni Conc. (mM) | Conjugate Size (kD) | Conjugate Ps-to-$CRM_{197}$ Ratio (w:w) | Percent Conjugated $CRM_{197}$ (%) |
|---|---|---|---|---|---|---|
| A | 43 | 0.17 | 1.5 | 3420 | 0.8 | 66 |
| B | 76 | 0.30 | 1.5 | 3280 | 0.8 | 60 |
| C | 250 | 0.98 | 1.5 | 3480 | 0.8 | 62 |

Based on these results, conjugation reactions were performed using multiple serotypes (Table 3) in the presence of 0.1 to 9 mM nickel chloride (preferably, 2 mM) to improve overall conjugation as measured by increased protein consumption. Ni (II) and nickel-cyanide complexes were subsequently cleared during the ultrafiltration steps that follow conjugation.

TABLE 3

Effect of nickel(II) on the extent of $CRM_{197}$ incorporated into conjugate for multiple serotypes.

| Serotype | Nickel Source | Nickel(II) Concentration in Conjugation Reaction (mM) | Percent Increase in Protein Conjugation (%), Relative to 0 mM Nickel(II) |
|---|---|---|---|
| 1 | nickel(II) chloride | 0 | 0 |
| | | 0.1 | 4 |
| | | 0.5 | 25 |
| | | 1 | 29 |
| | | 5 | 39 |
| 6B | nickel(II) sulfate | 0 | 0 |
| | | 1.5 | 50 |
| | | 9 | 50 |
| 7F | nickel(II) chloride | 0 | 0 |
| | | 2 | 24 |
| 9V | nickel(II) chloride | 0 | 0 |
| | | 2 | 10 |
| 18C | nickel(II) chloride | 0 | 0 |
| | | 2 | 106 |
| 22F | nickel(II) chloride | 0 | 0 |
| | | 2 | 37 |
| 23F | nickel(II) chloride | 0 | 0 |
| | | 2 | 21 |
| | | 5 | 26 |
| 33F | nickel(II) chloride | 0 | 0 |
| | | 2 | 27 |

In addition to Ni (II), several other metals including iron, aluminum, cobalt, copper, zinc, and silver were investigated. However, these were significantly less effective due to solubility limitations. In the case of copper, aggregation of $CRM_{197}$ was observed.

A 15 valent pneumococcal conjugate vaccine comprising polysaccharide-protein conjugates, all of which were made according to the processes of the invention, was found to be immunogenic in mice, rabbits, non-human primates and in humans (data not shown).

Example 4: Effect of pH and Temperature on Stability of Activated Serotype 3 Polysaccharide The effects of pH and temperature on activated serotype 3 polysaccharide size were studied to determine conditions for optimal polysaccharide stability. Optimal polysaccharide stability is desirable to minimize polysaccharide size reduction during the activation or conjugation reactions, enabling larger conjugates with less free polysaccharide.

Activated serotype 3 polysaccharide was prepared as described in Example 2. Following diafiltration against 10 mM potassium phosphate, pH 6.4, the activated polysaccharide solution was adjusted to pH 4.3 or 5.0 in 150 mM sodium acetate or pH 6.2, 6.9, or 7.7 in 150 mM potassium phosphate and stored at 2° C., 10° C., 23° C., or 35° C. After 10 hours, the solutions were assayed by HPSEC UV-MALS-RI to determine Ps size (Mw). Results are shown in FIG. 1.

Minimal Ps size reduction (<20%) was observed at pH 4.3-6.9 and 2-23° C. and at pH 4.3-6.2 and 2-35° C. Significant Ps size reduction (>50% size reduction) was observed at pH 6.9, 35° C. and pH 7.7, 23-35° C. These results support optimal periodate activation conditions and optimal conjugation conditions of pH 4.3-6.9 and 2-23° C. and at pH 4.3-6.2 and 2-35° C. for serotype 3 polysaccharide.

Example 5: Conjugation of Activated Serotype 3 Polysaccharide at pH 6.3, 10° C. and at pH 7.7, 35° C.

Based on the results in FIG. 1, conjugation reactions were conducted for activated serotype 3 polysaccharide, generated as described in Example 4. Following diafiltration against 10 mM potassium phosphate, the activated polysaccharide solution was adjusted to 150 mM potassium phosphate, pH 6.3 or pH 7.7. $CRM_{197}$ carrier protein was then added, targeting polysaccharide and protein concentrations of approximately 4.1 g/L and 6.8 g/L, respectively. The pH 6.3 solution was adjusted to either 0 mM or 2 mM nickel chloride. Sodium cyanoborohydride (2 mole per mole of polysaccharide repeating unit) was added to initiate conjugation. The pH 6.3 and pH 7.7 solutions were conjugated at approximately 10° C. and 35° C., respectively. After 48 hours, solutions were assayed by HPSEC UV-MALS-RI to determine conjugate size (Mw). Relative molecular weight results were normalized to the pH 6.3, 10° C., 2 mM nickel chloride results. Results are shown in Table 4.

TABLE 4

Conjugate size as a function of pH and temperature

| Conjugation conditions | Relative Conjugate Size after 48 hours |
|---|---|
| pH 6.3, 10° C., 2 mM nickel chloride | 1.00 |
| pH 6.3, 10° C., 0 mM nickel chloride | 0.88 |
| pH 7.7, 35° C., 0 mM nickel chloride | 0.27 |

The conjugation reactions conducted at pH 6.3, 10° C. yielded conjugates that were significantly larger (approximately 3-4 fold larger) than conjugate generated at pH 7.7, 35° C. These results are consistent with the polysaccharide stability results described in Example 4 and suggest that pH and temperature conditions for optimal Ps stability yield larger, more desirable conjugates.

What is claimed is:

1. A method for activating a *Streptococcus pneumoniae* serotype 3 polysaccharide for conjugation to a $CRM_{197}$ carrier protein comprising reacting a serotype 3 polysaccharide with periodate in an aqueous buffer (i) at a pH in the range from 4.3-6.9 and at a temperature in the range from 2-23° C., (ii) at a pH in the range from 4.3-7.7 and at a temperature in the range from 2-10° C., or (iii) at a pH in the range from 4.3-6.2 and at a temperature in the range from 2-35° C., wherein the activated serotype 3 polysaccharide detected after the reaction has a minimal (<20%) reduction in size (molecular weight).

2. The method of claim 1, wherein the periodate is sodium periodate.

3. The method of claim 1, wherein the reaction occurs at a pH in the range from 4.3-6.9 and at a temperature in the range from 2-23° C.

4. The method of claim 1, wherein the reaction occurs at a pH in the range from 4.3-7.7 and at a temperature in the range from 2-10° C.

5. The method of claim 1, wherein the reaction occurs at a pH in the range from 4.3-6.2 and at a temperature in the range from 2-35° C.

6. An activated serotype 3 polysaccharide prepared according to the method of claim 1.

7. A serotype 3 polysaccharide protein conjugate prepared with the activated serotype 3 polysaccharide of claim 6.

8. The conjugate of claim 7, wherein the protein is selected from the group consisting of tetanus toxoid, diphtheria toxoid and $CRM_{197}$.

9. The conjugate of claim 7, wherein the protein is $CRM_{197}$.

10. A multivalent pneumococcal conjugate vaccine composition comprising the serotype 3 polysaccharide protein conjugate of claim 7.

11. The vaccine composition according to claim 10 further comprising *Streptococcus pneumoniae* polysaccharide protein conjugates wherein the polysaccharide is selected from the following serotypes: 1, 4, 5, 6A, 6B, 7F, 9V, 14, 18C, 19A, 19F, 22F, 23F and/or 33F.

12. The vaccine composition of claim 11, wherein the protein is selected from the group consisting of tetanus toxoid, diphtheria toxoid and $CRM_{197}$.

13. The vaccine composition of claim 11, wherein the protein is $CRM_{197}$.

* * * * *